(12) United States Patent
Peine

(10) Patent No.: US 11,998,291 B2
(45) Date of Patent: Jun. 4, 2024

(54) ROBOTIC SURGICAL SYSTEMS WITH USER ENGAGEMENT MONITORING

(71) Applicant: Covidien LP, Mansfield, MA (US)

(72) Inventor: William J. Peine, Ashland, MA (US)

(73) Assignee: COVIDIEN LP, Mansfield, MA (US)

( * ) Notice: Subject to any disclaimer, the term of this patent is extended or adjusted under 35 U.S.C. 154(b) by 979 days.

(21) Appl. No.: 16/966,666

(22) PCT Filed: Jan. 2, 2019

(86) PCT No.: PCT/US2019/016241
§ 371 (c)(1),
(2) Date: Jul. 31, 2020

(87) PCT Pub. No.: WO2019/152771
PCT Pub. Date: Aug. 8, 2019

(65) Prior Publication Data
US 2021/0030498 A1    Feb. 4, 2021

Related U.S. Application Data

(60) Provisional application No. 62/625,714, filed on Feb. 2, 2018.

(51) Int. Cl.
*G06F 3/01* (2006.01)
*A61B 34/00* (2016.01)
(Continued)

(52) U.S. Cl.
CPC .............. *A61B 34/35* (2016.02); *A61B 34/20* (2016.02); *A61B 34/77* (2016.02); *A61B 90/37* (2016.02);
(Continued)

(58) Field of Classification Search
None
See application file for complete search history.

(56) References Cited

U.S. PATENT DOCUMENTS

2003/0060927 A1   3/2003  Gerbi et al.
2011/0118748 A1   5/2011  Itkowitz
(Continued)

FOREIGN PATENT DOCUMENTS

JP    2013022651 A    2/2013
KR    20130015437 A   2/2013
(Continued)

OTHER PUBLICATIONS

Japanese Office Action dated Feb. 2, 2023, issued in corresponding JP Applicaton No. 2020-541902, 6 pages.
(Continued)

*Primary Examiner* — Joseph R Haley
(74) *Attorney, Agent, or Firm* — Carter, DeLuca & Farrell, LLP

(57) ABSTRACT

A robotic surgical system with user engagement monitoring includes a robot assembly, a surgeon console, and a tracking device. The robot assembly includes a robotic arm coupled to a surgical instrument. The surgeon console includes a display device and a handle communicatively coupled to at least one of the robot assembly, the robotic arm, or the surgical instrument. The tracking device includes an image capture device configured to capture an image of a user position reference point. At least one of the surgeon console or the tracking device is configured to compute a position of the user position reference point based on the image; determine whether a user is engaged with the surgeon console based on the computed position; and, in response to a determination that the user is disengaged from the surgeon console, cause the robotic surgical system to operate in a safe mode.

14 Claims, 8 Drawing Sheets

(51) Int. Cl.
    *A61B 34/20*     (2016.01)
    *A61B 34/35*     (2016.01)
    *A61B 90/00*     (2016.01)
    *H04N 13/302*     (2018.01)

(52) U.S. Cl.
    CPC .... *H04N 13/302* (2018.05); *A61B 2034/2055* (2016.02); *A61B 2034/2065* (2016.02); *A61B 2090/371* (2016.02)

(56) References Cited

U.S. PATENT DOCUMENTS

| | | | |
|---|---|---|---|
| 2013/0030571 A1* | 1/2013 | Ruiz Morales | A61B 34/30 700/259 |
| 2014/0024889 A1 | 1/2014 | Xiaoli | |
| 2014/0121834 A1 | 5/2014 | Ogawa et al. | |
| 2017/0329402 A1* | 11/2017 | Riedel | H04N 13/337 |
| 2017/0367773 A1 | 12/2017 | Kottenstette et al. | |
| 2019/0144003 A1* | 5/2019 | Hyuga | G06V 40/193 340/425.5 |
| 2020/0015917 A1* | 1/2020 | Cavalier | B25J 9/1689 |
| 2020/0268455 A1* | 8/2020 | Zheng | A61B 8/0841 |

FOREIGN PATENT DOCUMENTS

| | | |
|---|---|---|
| KR | 10-2016-0124058 A | 10/2016 |
| KR | 101802464 B1 | 11/2017 |
| WO | 2008049898 A1 | 5/2008 |
| WO | 2012127404 A2 | 9/2012 |
| WO | 2013018983 A1 | 2/2013 |
| WO | 2017210101 A1 | 12/2017 |

OTHER PUBLICATIONS

Extended European Search Report dated Feb. 10, 2022 corresponding to counterpart Patent Application EP 19747135.2.

Chinese Office Action dated May 19, 2023, issued in corresponding CN Appln. 201980001014, 13 pages.

Partial European Search Report dated Oct. 27, 2021 corresponding to counterpart Patent Application EP 19747135.2.

International Search Report dated May 21, 2019 and Written Opinion completed May 21, 2019 corresponding to counterpart Int'l Patent Application PCT/US2019/016241.

* cited by examiner

ROBOTIC SURGICAL SYSTEMS WITH USER ENGAGEMENT MONITORING

BACKGROUND

Robotic surgical systems have grown in popularity, and the ergonomics and comfort in using robotic surgical systems have improved through an open-console architecture. In contrast to a closed-console architecture, which requires a surgeon to place her head within an immersive display apparatus to operate the robotic surgical system, an open-console architecture enables the surgeon to use the surgeon console while maintaining more open communication with other surgeons and staff in the operating room. The open-console architecture also enables the surgeon to be more aware of events occurring within the operating room and places the surgeon in a better position to handle emergency situations that may arise during the course of a surgical procedure.

With the open-console architecture, however, the surgeon may become distracted from engagement with the surgeon console more easily than they may be with a closed-console architecture. Robotic surgical systems having an open-console architecture, therefore, may carry increased safety risks. Accordingly, systems, devices, and methods are needed to mitigate safety risks stemming from surgeon distraction from engagement with robotic surgical systems.

SUMMARY

In one aspect, this disclosure describes a robotic surgical system with user engagement monitoring. The robotic surgical system includes a robot assembly, a surgeon console, and a tracking device. The robot assembly includes a robotic arm coupled to a surgical instrument. The surgeon console includes a handle and a display device. The handle is communicatively coupled to at least one of the robot assembly, the robotic arm, or the surgical instrument. The tracking device includes an image capture device configured to capture an image of a user position reference point. At least one of the surgeon console or the tracking device is configured to compute, based on the captured image, a position of the user position reference point relative to the display device; determine whether a user is engaged with or disengaged from the surgeon console based on the computed position; and, in response to a determination that the user is disengaged from the surgeon console, cause the robotic surgical system to operate in a safe mode.

In embodiments, at least one of the surgeon console or the tracking device is further configured to compute the position of the user position reference point by generating location data corresponding to at least one of the position, or an orientation, of the user position reference point, within a three dimensional coordinate space, relative to the display device.

In embodiments, in the determination of whether the user is engaged with or disengaged from the surgeon console, at least one of the surgeon console or the tracking device is further configured to compute a difference angle based on the position and orientation of the user position reference point relative to the display device; compare the difference angle to a first threshold angle; and, in response to a determination that the difference angle is greater than the first threshold angle, determine that the user is disengaged from the surgeon console.

In embodiments, at least one of the surgeon console or the tracking device is further configured to select the first threshold angle from a plurality of first threshold angles based on the position and the orientation of the user position reference point relative to the display device.

In embodiments, at least one of the surgeon console or the tracking device is further configured to compute, based on the position and the orientation of the user position reference point, a direction of movement of the user position reference point relative to the display device; and select the first threshold angle based on the direction of movement of the user position reference point.

In embodiments, in the determination of whether the user is engaged with or disengaged from the surgeon console, at least one of the surgeon console or the tracking device is further configured to, in response to a determination that the difference angle is less than the first threshold angle, determine whether the difference angle is less than a second threshold angle that is smaller than the first threshold angle; and, in response to a determination that the difference angle is less than the second threshold angle, determine that the user is engaged with the surgeon console.

In embodiments, at least one of the surgeon console or the tracking device is further configured to, in response to the determination that the user is engaged with the surgeon console, cause the robotic surgical system to exit the safe mode.

In embodiments, at least one of the surgeon console or the tracking device is further configured to, at a time when the robotic surgical system operates in the safe mode and in response to a determination that the user is engaged with the surgeon console, cause the robotic surgical system to exit the safe mode after an elapsing of a threshold amount of time after the determination that the user is engaged.

In embodiments, the robotic surgical system further comprises a computing device. At least one of the surgeon console or the tracking device is further configured to, at a time when the robotic surgical system operates in the safe mode, restrict movement of the handle from a previous position of the handle; and transmit, to the computing device, instructions to restrict movement of at least one of the robot assembly, the robotic arm, or the surgical instrument. The computing device is configured to receive the instructions and transmit the instructions to at least one of the robot assembly, the robotic arm, or the surgical instrument. At least one of the robotic arm, the robot assembly, or the surgical instrument is configured to receive the instructions, and restrict movement of at least one of the robot assembly, the robotic arm, or the surgical instrument in response to the instructions.

In embodiments, at least one of the surgeon console or the tracking device is further configured to, at a time when the robotic surgical system operates in the safe mode, prevent a movement of the handle from causing a corresponding movement of the robotic arm communicatively coupled to the handle.

In embodiments, at least one of the surgeon console or the tracking device is further configured to detect an amount of movement of the handle; determine, based on the amount of movement of the handle, an amount of movement of at least one of the robot assembly, the robotic arm, or the surgical instrument to be caused in response to the movement of the handle; and cause at least one of the robot assembly, the robotic arm, or the surgical instrument to move by the determined amount of movement. At a time when the robotic surgical system operates in the safe mode, the determination of the amount of movement of at least one of the robot assembly, the robotic arm, or the surgical instrument to be caused includes applying a downward scaling factor.

In embodiments, at least one of the surgeon console or the tracking device is further configured to compute a velocity of a movement of the handle and modify the downward scaling factor based on the velocity.

In embodiments, the surgeon console includes a plurality of motors corresponding to the handle, each of the motors being operably coupled to the handle and being associated with a direction of movement of the handle. At a time when the robotic surgical system operates in the safe mode, at least one of the surgeon console or the tracking device is further configured to compute a velocity of a movement of the handle; compute a direction of the movement of the handle; compute, based on the velocity of the movement of the handle, a force in a direction opposite to the direction of the movement of the handle; identify, among the plurality of motors of the handle, a motor associated with the direction opposite to the direction of the movement of the handle; and cause actuation of the identified motor in the direction opposite to the direction of the movement of the handle to generate the computed force in the direction opposite to the direction of the movement of the handle.

In embodiments, the surgeon console further comprises a plurality of motors operably coupled to the handle and associated with a plurality of directions, respectively, of movement of the handle. At least one of the surgeon console or the tracking device is further configured to, in response to the determination that the user is disengaged with the surgeon console, identify a first position of the handle; compute a distance traveled by the handle from the first position of the handle; compute a direction of the movement of the handle; compute, based on the distance, a force in a direction opposite to the direction of the movement of the handle; identify, among the plurality of motors of the handle, a motor associated with the direction opposite to the direction of the movement of the handle; and cause actuation of the identified motor in the direction opposite to the direction of the movement of the handle to generate the computed force in the direction opposite to the direction of the movement of the handle.

In embodiments, the surgeon console is further configured to actuate the motor in the direction opposite to the direction of the movement of the handle until the handle is positioned in the first position.

In embodiments, the robotic surgical system further comprises eyewear including a plurality of markers, and the user position reference point includes at least one of the plurality of markers.

In embodiments, the user position reference point includes at least one of an eye, a head, or another portion of the user.

In embodiments, the display device is an autostereoscopic display device.

According to another aspect, the present disclosure describes another robotic surgical system with user engagement monitoring. The robotic surgical system includes a robot assembly and a surgeon console. The robot assembly includes a robotic arm coupled to a surgical instrument. The surgeon console includes a handle communicatively coupled to at least one of the robot assembly, the robotic arm, or the surgical instrument. The handle includes at least one of a capacitive sensor or an optical sensor. The surgeon console is configured to receive, from at least one of the capacitive sensor or the optical sensor, data related to contact with the handle by a user; determine, based on the data related to contact with the handle, whether the user is engaged with or disengaged from the surgeon console; and, in response to a determination that the user is disengaged from the surgeon console, cause the robotic surgical system to operate in a safe mode.

In embodiments, the surgeon console is further configured to, in the determination of whether the user is disengaged from the surgeon console, determine that the user is disengaged from the surgeon console in response to the data related to the contact with the handle indicating that the user is not in contact with the handle.

BRIEF DESCRIPTION OF THE DRAWINGS

Various aspects and features of robotic surgical systems and methods of the present disclosure are described herein below with references to the drawings, wherein.

DETAILED DESCRIPTION

Figure 1A:
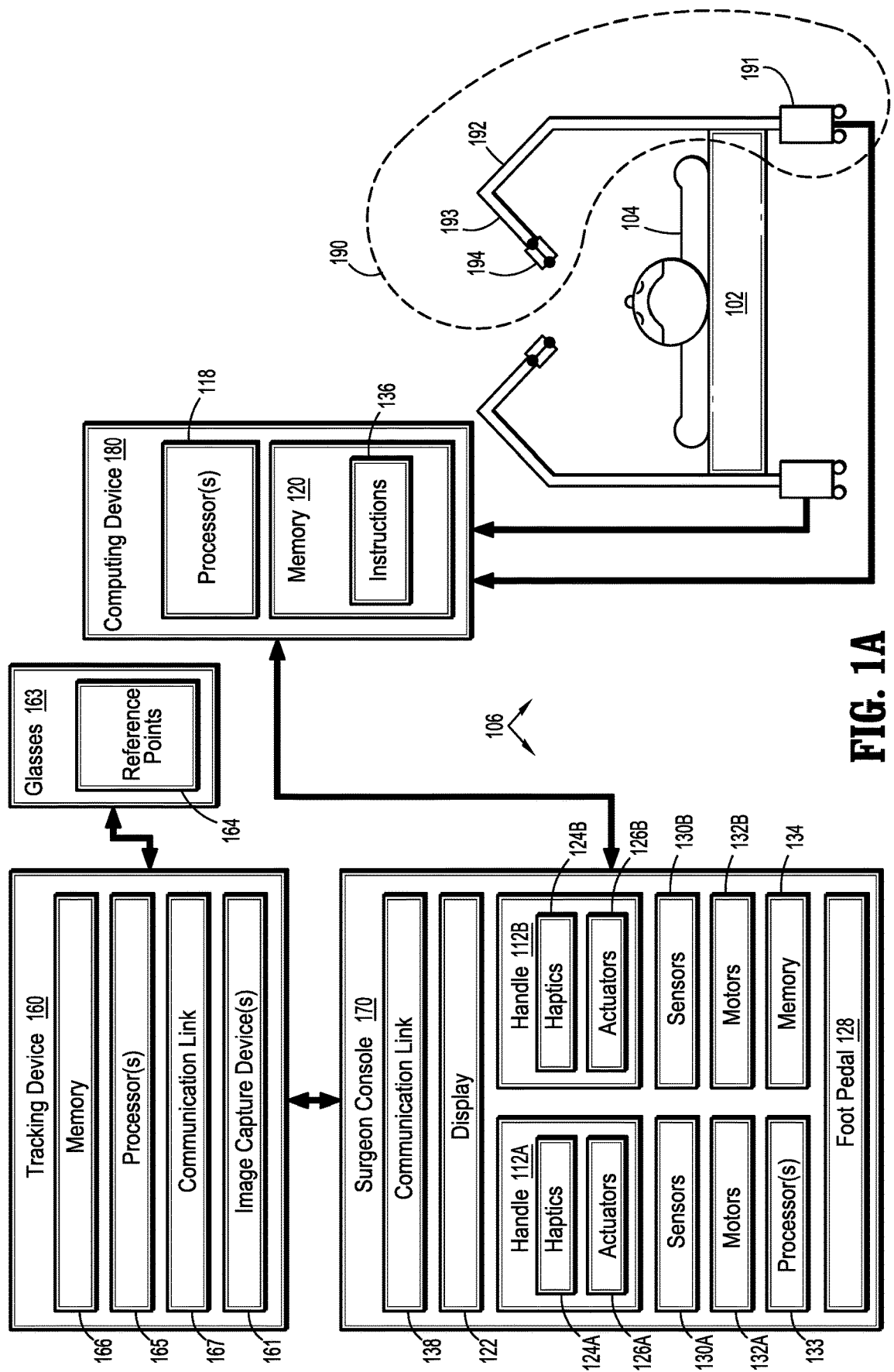
FIG. 1A illustrates an exemplary robotic surgical system, in accordance with an illustrative embodiment herein.

The present disclosure is directed to robotic surgical systems, devices, methods, and computer-readable media that mitigate safety risks stemming from surgeon distraction from engagement with robotic surgical systems during surgical robotic procedures. More particularly, the present disclosure relates to systems and methods for identifying disengagement of a user using the robotic surgical system and causing the robotic surgical system to operate in one or more safe modes when the user is disengaged, thereby mitigating the risk that the user unintentionally injures the patient or otherwise compromises the surgical procedure by actuating the robotic surgical system while distracted. The systems and methods described herein provide various techniques for tracking a user position relative to a display of a surgeon console and, based on the tracked user position, determining whether the user is disengaged from a surgeon console, even for open-console architectures. If the user is disengaged from the surgeon console, the robotic surgical system is operated in one or more safe modes. Utilizing the technologies, techniques, and embodiments described herein, users are provided with a safer operating environment in which to perform robotic surgeries, and patients are afforded a safer environment in which to receive surgical treatment via robotic surgical systems.

Embodiments of the present disclosure are now described in detail with reference to the drawings in which like reference numerals designate identical or corresponding elements in each of the several views. As used herein, the terms "user" and "clinician" refer to a doctor, a surgeon, a nurse, technician, medical assistant, or similar support personnel or any other person that may use the robotic surgical systems described herein. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

FIG. 1A shows an example robotic surgical system 100 in accordance with an exemplary embodiment herein. In general, the surgical system 100 is configured to determine whether or not a user is engaged with a surgeon console of the surgical system 100 and, based on that determination, operate in one of various operational modes in which the system is configured to operate, including one or more safe modes and one or more non-safe modes, which are also referred to as normal modes. As shown in FIG. 6 and described below, the types of safe modes in which the system 100 is configured to operate include, but are not limited to (1) a safe mode based on locking a handle and a robot assembly of the surgical system 100, (2) a safe mode based on preventing handle movement from causing corresponding robot assembly movement, (3) a safe mode based on a velocity of handle movement, (4) a safe mode based on handle velocity-based opposing force, and (5) a safe mode based on position-based opposing force. Additional details of determining whether a user is engaged with, or disengaged from, the robotic surgical system 100 and, in response, causing the surgical system 100 to operate in non-safe modes or safe modes are provided herein in the context of FIGS. 2 through 7. The specific number of components of the system 100 depicted in FIG. 1A and the arrangement and configuration thereof are provided for illustrative purposes only, and should not be construed as limiting. For instance, various embodiments herein employ fewer or greater than all of the components shown in FIG. 1A. Additionally, the system 100 depicted in FIG. 1A is provided as an illustrative context in which various exemplary embodiments herein are applicable.

The system 100 includes an operating table 102 upon which a patient 104 lies during a surgical procedure, a tracking device 160, a surgeon console 170 with which a user interacts during the surgical procedure, a computing device 180, and one or more robot assemblies 190. The tracking device 160, surgeon console 170 and the computing device 180 are communicatively coupled to one another and the one or more robot assemblies 190 by way of communication paths 106, which, in various embodiments herein, may be implemented as wired communication paths and/or as wireless communication paths.

Each of the one or more robot assemblies 190 includes multiple subunits 191, 192, 193, and 194. The subunit 191 is a cart unit, the subunit 192 is a setup arm unit, the subunit 193 is a robot arm unit, and the subunit 194 is an instrument drive unit. The subunits 191, 192, 193, 194, are operably coupled to each other directly or indirectly, and communicatively coupled to each other directly or indirectly by way of one or more communication paths (not shown in FIG. 1A). The cart unit 191 is arranged adjacent to the operating table 102 within range of the patient 104 undergoing the surgical procedure and is configured to move along side of the operating table 102 or the patient 104 and towards and away from the operating table 102 or the patient 104. The instrument drive unit 194 is couplable to one or more corresponding surgical instruments (not shown in FIG. 1A), and/or image capture devices (not shown in FIG. 1A) that may be interchangeably fastened thereto depending on the particular surgical procedure being performed. Exemplary types of surgical instruments include, but are not limited to, a probe, an end effector, a grasper, a knife, scissors, and/or the like. Exemplary types of the image capture devices include, but are not limited to, endoscopic cameras, laparoscopic cameras, any type of image capture apparatuses, or instruments coupled to image capture apparatuses.

The computing device 180 includes one or more processors 118 and one or more memory units 120, and the one or more processors 118 are operably coupled to the one or more memory units 120. In various embodiments, the computing device 180 may be integrated with the surgeon console 170, or may be a standalone device, such as a computing tower, disposed within or near the operating room. The one or more processors 118 may be any type of suitable processor that is adapted to perform or execute the techniques or operations or instructions described herein. The one or more memory units 120 store instructions, such as instructions 136 (in an example, software), to be executed by the one or more processors 118, and the techniques described herein are performed by the computing device 180 in response to the one or more processors 118 executing the instructions stored in the one or more memory units 120. The one or more memory units 120 may be any type of hardware device suitable to store machine instructions, data, and/or the like.

The surgeon console 170 includes a communication link 138, a display device 122, one or more handles 112A, 112B (collectively, handle(s) 112), one or more processors 133, one or more memory units 134, a foot pedal 128, and at least one motor corresponding to directions in which the handle 112 is configured to move, such as motors 132A for handle 112A and motors 132B for handles 112B. The display device 122 may be a touch display, or include a touch screen, which is configured to receive inputs via a user's touch. In some embodiments, the display device 122 is configured to display a graphical user interface (GUI) configured to receive inputs for various settings of the surgical system 100 including, but not limited to, settings for safe modes and threshold data used in determining whether a user is disengaged with the surgeon console 170. The display device 122 may be configured to display images received by the surgeon console 170, including images related to the surgical site on or within the patient 104 from an image capture device coupled to the robot assembly 190. In some embodiments, the display device 122 is a two-dimensional (2D) display device. In some embodiments, the display device 122 is configured to display one or more stereoscopic images received by the surgeon console 170 to allow a user to view the one or more stereoscopic images as three-dimensional (3D) images. In some embodiments, the display device 122 is an autostereoscopic display device.

The user interacts with the surgeon console 170 using the handles 112 during a surgical procedure. In some embodiments, the handle 112A is a left handle and the handle 112B is a right handle, operated upon by a left hand and right hand, respectively, of the user. The handle 112A, in some embodiments, includes various haptics 124A and/or actuators 126A, which provide feedback to the user relating to various tissue parameters or conditions, such as, tissue resistance due to manipulation, cutting, or otherwise treating, pressure by the instrument onto the tissue, tissue temperature, tissue impedance, and/or the like. Similarly, the handle 112B, in some embodiments, includes various haptics 124B and/or actuators 126B, which are configured similar to as haptics 124A and/or actuators 126A. The haptics 124A and 124B are referred to herein collectively as haptics 124. The actuators 126A and 126B are referred to herein as collectively as the actuators 126. As can be appreciated, such haptics 124 provide the surgeon with enhanced tactile feedback simulating actual operating conditions. The haptics 124 may include vibratory motors, electroactive polymers, piezoelectric devices, electrostatic devices, subsonic audio wave surface actuation devices, reverse-electrovibration, or any other device capable of providing a tactile feedback to a user. As mentioned above, the handles 112 may also include a variety of different actuators 126, which, for instance, may be employed for delicate tissue manipulation and/or treatment further enhancing the surgeon's ability to mimic actual operating conditions.

The surgeon console 170 includes one or more sensors 130A and 130B (collectively, 130) that are operably coupled to a handle 112. For example, the sensors 130A may be operably coupled to the handle 112A and the sensors 130B may be operably coupled to the handle 112B. One or more of the sensors 130A and 130B may be configured to determine metrics related to the motions of the handles to which they are operably coupled. Exemplary types of the metrics related to the motions of the handles 112 include, but are not limited to, a direction of movement of the handles 112, a velocity of movement of the handles 112, a distance of movement of the handles 112, and/or the like. In some embodiments, the surgeon console 170 transmits the metrics data related to the motions of the handles 112 to the computing device 180 and/or robot assemblies of the surgical system 100, such as the robot assembly 190. One or more of the sensors 130A and 130B may be a capacitive sensor and/or an optical sensor and the surgeon console 170 may be configured to determine whether a user is in contact with the handle 112A or the handle 112B based on the data received from the capacitive sensors and/or the optical sensors of the sensors 130A and 130B.

Each of the handles 112 is operably coupled to and associated with at least one motor for each direction of movement in which the handle 112 is configured to move. Examples of such motors are motors 132A and motors 132B (collectively, motors 132) for the handle 112A and the handle 112B, respectively. Each motor of motors 132A is operably coupled to the handle 112A and each motor of the motors 132A is associated with a direction of movement in which the handle 112A is configured to move. Similarly, each motor of motors 132B is operably coupled to handle 112B and each motor of the motors 132B is associated with a direction of movement in which the handle 112B is configured to move. Each motor of the motors 132 associated with a direction is configured to actuate in the associated direction to cause movement of the handle 112 in the associated direction, and to actuate in a direction opposite to their associated direction to resist the movement of the handle 112 in the associated direction. For example, if handle 112A is configured to move in a left direction then at least one motor of the motors 132A is associated with the left direction. If it is desired that the handle 112A should be moved in the left direction, then the surgeon console 170 actuates the motor associated with the left direction in a direction that corresponds to the left direction in order to assist in the movement of the handle 112A in the left direction, and if it is desired that the movement of the handle 112A in the left direction should be resisted, then the surgeon console 170 actuates the motor associated with the left direction in a direction that corresponds to a direction opposite to the left direction in order to resist the movement of the handle 112A in the left direction. The motors 132 are configured to be actuated at various speeds.

The foot pedal 128 is configured to receive one or more inputs from a user to the surgeon console 170. The foot pedal 128 is configured to be placed into two or more positions and a position of the foot pedal 128 is associated with an input to the surgeon console 170. The selection of a position of the foot pedal 128 provides the associated input to the surgeon console 170. In some embodiments, users provide inputs to update settings and/or configuration data related to one or more components of the surgical system 100 using the foot pedal 128. The surgeon console 170 is configured to update settings and/or configuration data based on the inputs received via the foot pedal 128, and transmit the updated settings and/or configuration data to the computing device 180 and/or the one or more robot assemblies, such as the robot assembly 190. In some embodiments, one of the positions of the foot pedal 128 is configured to be a rest position of the foot pedal 128, and an input signal that indicates that the foot pedal 128 is in the rest position is transmitted to the surgeon console 170 when the foot pedal 128 is in the rest position. In some embodiments, the foot pedal 128 is a momentary foot pedal switch and inputs to the surgeon console 170 are transmitted based on a sequence of interrogations with the foot pedal 128, such as double tapping the foot pedal 128. The surgeon console 170 transmits the inputs received via the foot pedal 128 to the computing device 180 and/or the robot assemblies of the surgical system 100, such as robot assembly 190.

Although FIG. 1A shows the tracking device 160 and the surgeon console 170 as being separate components communicatively coupled to one another via communication paths and the communication links 138, 167, this configuration is merely provided as an illustrative example. In other embodiments, the tracking device 160 is integrated into the surgeon console 170. Accordingly, functionality described herein as being performed by the tracking device 160 and/or by the surgeon console 170 may, in various other embodiments, be performed by the tracking device 160, by the surgeon console 170, by any combination thereof, and/or by any combination of components thereof, such as the processors 133 or 165 and/or memories 134 or 166.

Figure 1B:
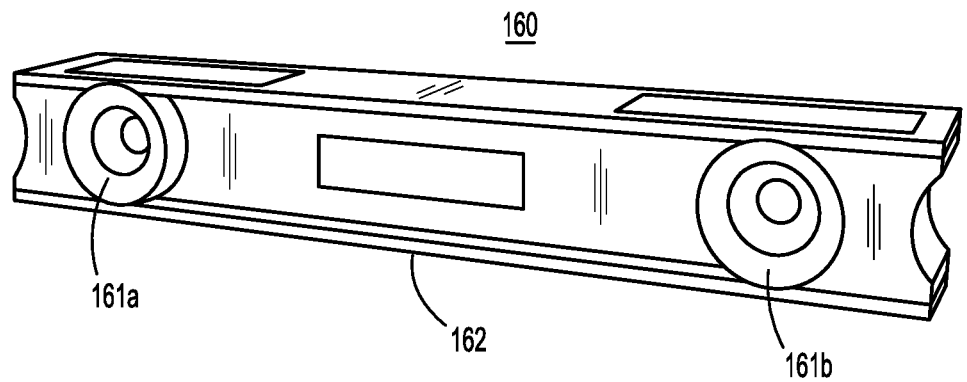
FIGS. 1B and 1C illustrate an exemplary optical tracking device of the robotic surgical system of FIG. 1.

In one embodiment, the tracking device 160 includes one or more image capture devices 161, one or more processors 165, one or more memories 166, and one or more communication links 167. The surgeon console 170 is configured to, in real-time or near real-time, identify and track a user position reference point (for example, a portion of a user or of eyewear 163 worn by the user); determine whether the user is engaged with, or disengaged from, the surgeon console 170; and cause the surgical system 100 to operate in a non-safe mode or a safe mode based on a result of the determination. As used herein, the term user position reference point generally refers to at least a portion of the user and/or at least a portion of an object (such as eyeglasses) that the surgeon console 170 can utilize as a basis upon which to compute and/or track a position and/or an orientation of the user relative to a reference coordinate system, such as a coordinate system defined by a front plane of the display device 122 facing the user. In various embodiments, the user position reference point may include a single portion of the user or the object or include multiple portions of the user or the object. As used herein in this context, the term "a portion of a user" refers to any anatomical part of a user, including but not limited to, an eye, a pupil within an eye, a head, a face, and/or the like. Exemplary types of the one or more image capture devices 161 are image capture devices 161a and 161b, illustrated in FIG. 1B. As shown in FIG. 1B, the image capture devices 161a and 161b are positioned apart from each other. The surgeon console 170 is configured to cause the image capture devices 161 to move to track the user portion reference point over one or more time periods. In some embodiments, the one or more image capture devices 161 are housed within a housing unit, such as housing unit 162, and the housing unit 162 is included within or attached to the surgeon console 170.

Figure 1C:
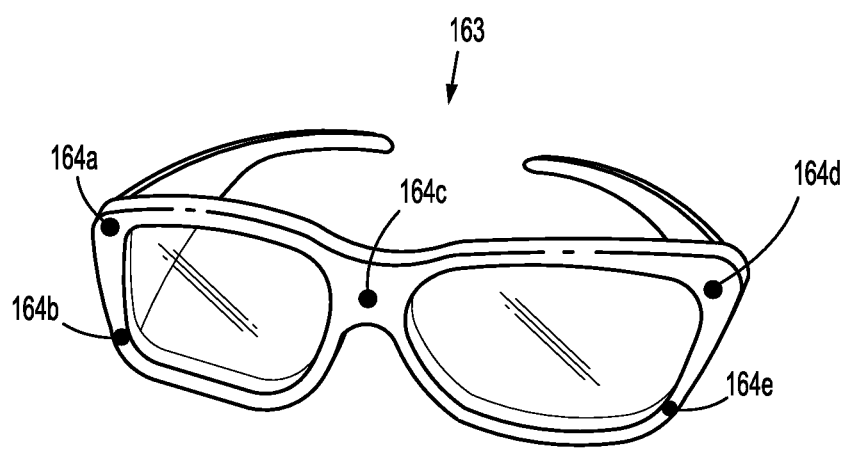

In some embodiments, the surgeon console 170 is trained on one or more facial and/or feature recognition algorithms and is configured to detect eyes, pupils, a head, a face, and/or the like of a user by applying the one or more facial and/or feature recognition algorithms on one or more images captured by the image capturing devices 161. In some embodiments, the surgeon console 170 is configured to perform optical tracking of the user position reference point, and the one or more image capture devices 161 are equipped with infrared (IR) pass filters (not shown in FIGS. 1A-1C) in front of their lenses and a ring of IR light emitting diodes (LEDs) (not shown in FIGS. 1A-1C) around the lens. In optically tracking the user position reference point, the surgeon console 170 periodically illuminates a desired space with IR light using the IR LEDs, and identifies and tracks a the user position reference point by detecting the IR light reflections from markers placed on a portion of the user or on an object, such as the eyewear 163, worn by the user, using the one or more image capture devices 161. An exemplary type of the eyewear 163 including markers 164a, 164b, 164c, 164d, 164e, (collectively, 164), which may be reflective markers, positioned thereon is illustrated in FIG. 1C.

The surgeon console 170 includes one or more processors 133 and one or more memory units 134. The one or more processors 133 are operably coupled to the one or more memory units 134. The one or more processors 133 may be any type of suitable processor that is adapted to perform or execute the techniques or operations or instructions described herein. The one or more memory units 134 store instructions (not shown in FIG. 1A) to be executed by the one or more processors 133, and the techniques described herein may be performed by the surgeon console 170 in response to the one or more processors 133 executing the instructions stored in the one or more memory units 134. The one or more memory units 134 may be any type of hardware device suitable to store machine instructions, data, and/or the like.

The processors 118, 133, 165 and the processors (not shown in FIG. 1A) of the robot assemblies 190 (collectively, processors of the surgical system 100) may be hardware processors programmed to perform the techniques described herein pursuant to the instructions in firmware, memory, or other storage, or a combination thereof. Similarly, the processors of the surgical system 100 may also be one or more application specific integrated circuits (ASICs), field programmable gate arrays (FPGAs) that are persistently programmed to perform the techniques or operations described herein. The processors of surgical system 100 may also be a central processing unit (CPU), a digital signal processor (DSP), a microprocessor, or any other device that incorporates hard wired logic or program logic or both to perform the operations or techniques described herein.

The memory units 120, 134, 166 and the memory units (not shown in FIG. 1A) of the robot assemblies 190 (collectively, memory units of the robotic surgical system 100) may be volatile memory, such as random access memory (RAM) (e.g., dynamic random access memory (DRAM), static random access memory (SRAM), and/or the like). The memory units of robotic surgical system 100 may be non-volatile memory, such as read-only memory (ROM) (e.g., programmable read-only memory (EPROM), electrically erasable programmable read-only memory (EEPROM), non-volatile RAM (NVRAM), and/or the like). The memory units of the surgical system 100 may also be magnetic, optical, or electrical media. As will be appreciated, the processors and the memory units of the robotic surgical system 100 implementation is provided by way of example only, and should not be construed as limiting. For instance, procedures of any of the embodiments of the present disclosure may be implemented by hardware components, firmware components, software components, and/or any combination thereof.

Figure 2A:
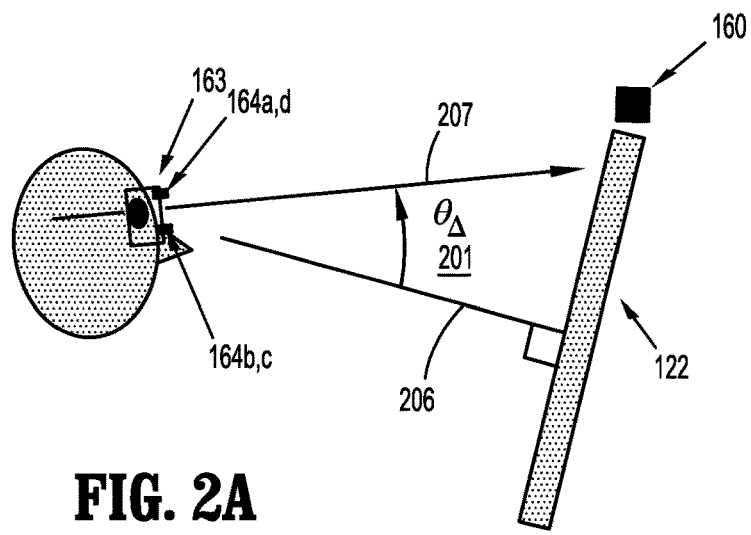
FIGS. 2A-2C illustrate exemplary aspects of how the robotic surgical system of FIG. 1 may be used to monitor user engagement.

Turning now to FIG. 2A, an exemplary arrangement of the display device 122 and the one or more image capture devices 161 is shown in accordance with one or more embodiments herein. The one or more image capture devices 161 are positionally affixed to the display device 122 such that the positional relationship between the image capture devices 161 and the display device 122 is known, and the surgeon console 170, the tracking device 160, and/or the computing device 180 are configured to determine whether a user is engaged with, or disengaged from, the surgeon console 170 based in part on the positional relationship between the image capture devices 161 and the display device 122. In some embodiments, the positional relationship between the image capture devices 161 and the display device 122 is provided as an input to the surgeon console 170, for example, by a user. The surgeon console 170 may be configured to compute the positional relationship between the one or more image capture devices 161 and the display device 122, based on the orientation of the display device 122 relative to a fixed location of the environment in which the surgeon console 170 is placed, such as the ground or floor of a room.

In tracking the user position reference point in real-time and over one or more time periods, the surgeon console 170 computes a location of the user position reference point relative to the display device 122 in each of the time periods. The location of the user position reference point relative to the display device 122 is computed based in part on data related to the positional relationship between the one or more image capture devices 161 and the display device 122. In computing the location of the user position reference point relative to the display device 122, the surgeon console 170 computes a position and an orientation of the user position reference point. The position of the user position reference point is computed in a three-dimensional coordinate space, for example, in an x, y, and z coordinate space, and the orientation of the user position reference point is computed by computing the roll, pitch, and yaw angles of the user position reference point. The position and the orientation of the user position reference point are computed relative to the display device 122.

Figure 2B:
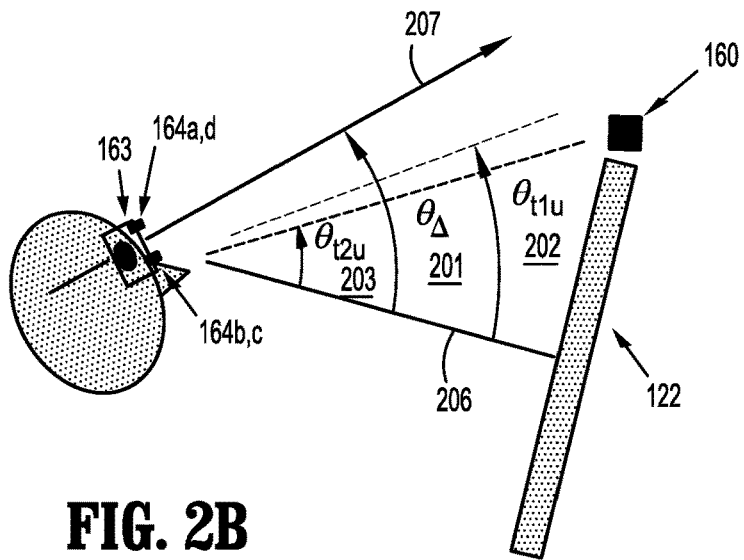
Figure 2C:
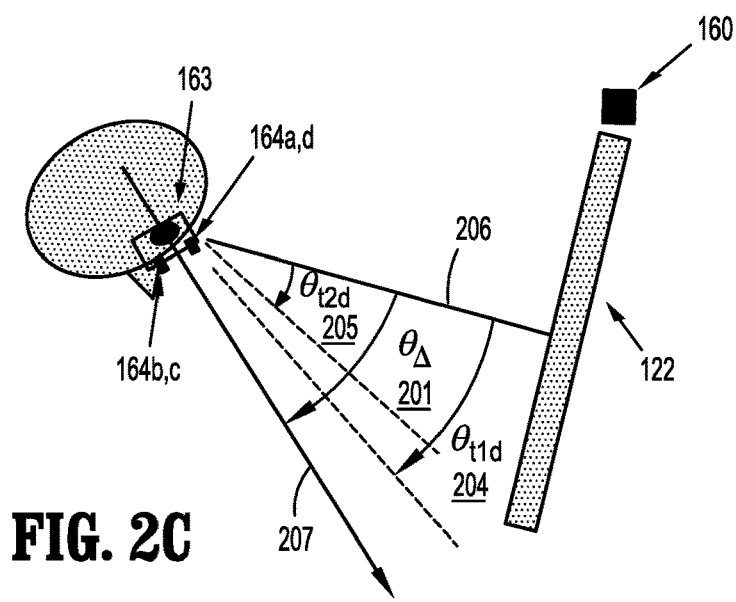

Using the position and the orientation of the user position reference point, the surgeon console 170 computes a difference angle $\theta_A$. As used herein, the term "difference angle" is an angle between an imaginary line 206 normal or perpendicular to a front plane of the display device 122 and an imaginary line 207 normal to a plane formed by user position reference point(s) (for example, three user position reference points corresponding to three of the markers 164) being tracked. An example of such a difference angle $\theta_A$ is shown as difference angle $\theta_A$ 201 in FIG. 2A. The normal imaginary line 207 is substantially aligned with a direction in which the surgeon is looking. In the example of FIG. 2A, FIG. 2B, FIG. 2C, a user is wearing the eyewear 163, which has the markers 164 positioned thereon, at least three markers 164 of which represents the user position reference points, and the surgeon console 170 is performing optical tracking of the user position reference points. The surgeon console 170 computes the difference angle $\theta_A$ 201 by computing a relative angle between the imaginary line 207 normal to the plane formed by the markers 164 and the imaginary line 206 normal to the front plane of the display device 122.

As the user's head moves, the position of the imaginary line 207 normal to the plane formed by the markers 164 changes from a first position (for example, the position shown in FIG. 2A) to a second position (for example, the positions shown in FIG. 2A or FIG. 2B), and accordingly the difference angle $\theta_A$ 201 changes, as shown in FIG. 2B and FIG. 2C. In embodiments where the surgeon console 170 is tracking the user position reference points by detecting features of the user, such as the eyes of the user, the surgeon console 170 computes the difference angle $\theta_A$ 201 by computing a position of an imaginary line (not shown in FIGS. 2A-2C) normal to the detected features of the user and a position of the imaginary line 206 normal to the front plane of the display device 122, and by computing an angle between the computed positions of the two imaginary lines. As the detected features move relative to the display device 122, the position of the imaginary line normal to the detected features changes and the difference angle $\theta_A$ 201 changes accordingly.

The surgeon console 170 is configured to determine whether the user is engaged with, or disengaged from, the surgeon console based in part on the difference angle $\theta_A$ 201. Additional details of the determination by the surgeon console 170 as to whether the user is engaged with, or disengaged from, the surgeon console 170 are provided herein in the contexts of FIG. 3, FIG. 4, and FIG. 5.

Figure 3:
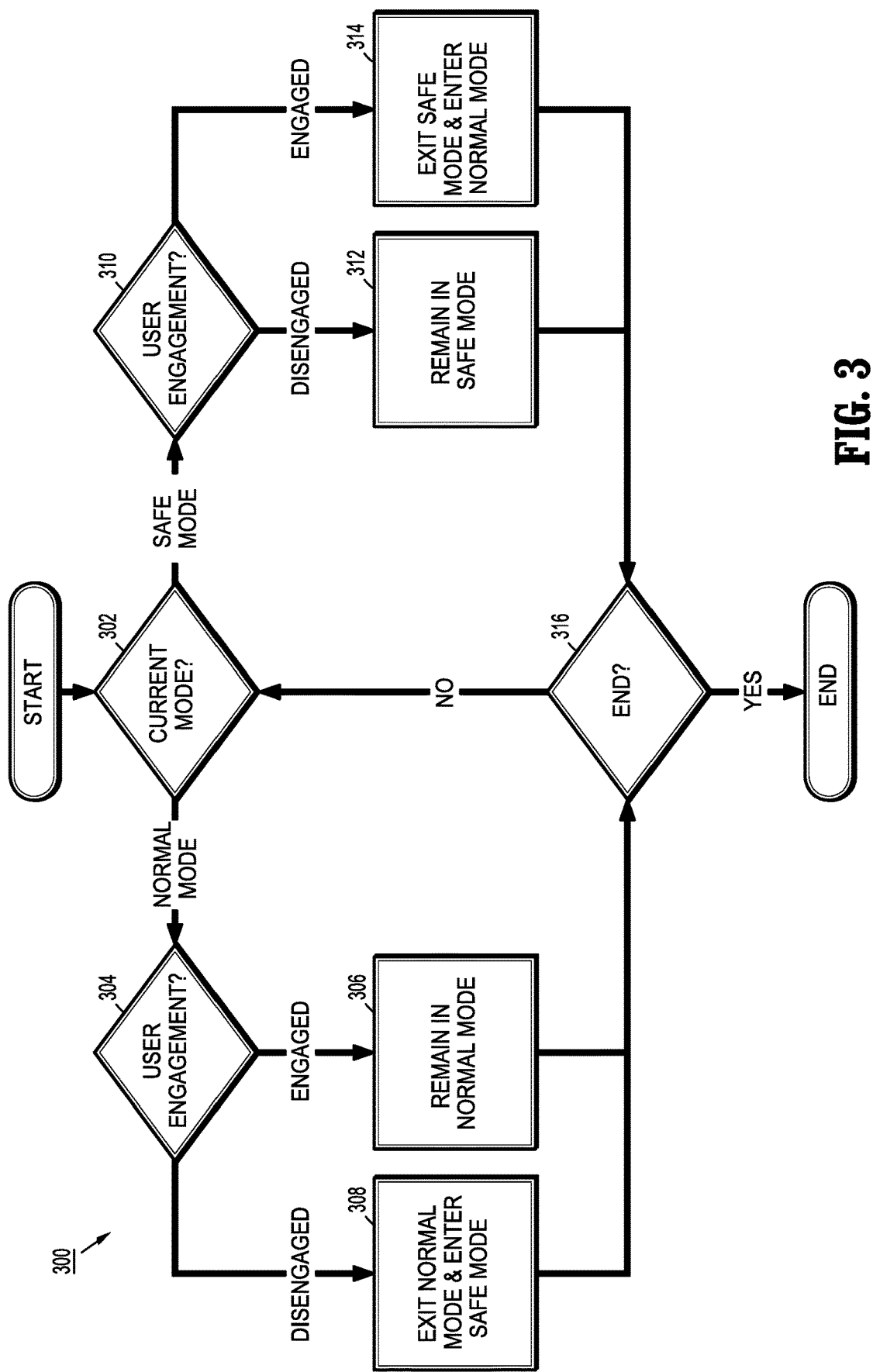
FIG. 3 is a flowchart that illustrates an exemplary method for controlling an operational mode of the robotic surgical system of FIG. 1 based on whether a user is engaged with, or disengaged from, the surgeon console thereof.

FIG. 3 illustrates a method for controlling an operational mode of the robotic surgical system 100 based on whether a user is engaged with, or disengaged from, the surgeon console 170, in accordance with an exemplary embodiment herein. At step 302, the surgeon console 170 determines a mode in which the surgeon console 170 is currently operating, such as a safe mode or a normal mode (any mode other than a safe mode). If the surgeon console 170 determines that the surgeon console 170 is currently operating in a normal mode ("NORMAL MODE" at step 302) then processing proceeds to block 304. At block 304, the surgeon console 170 determines whether the user is engaged with, or disengaged from, the surgeon console 170. Exemplary aspects of how the surgeon console 170 makes the determination at step 304 are provided below in connection with FIG. 4 and FIG. 5. In general, the surgeon console 170 may determine whether the user is engaged with, or disengaged from, the surgeon console 170 by tracking a user's head or eye position (for instance, relative to the display device 122), hand position (for instance, contact with handle(s) 112), or any combination thereof. If the surgeon console 170 determines that the user is engaged with the surgeon console 170 ("ENGAGED" AT BLOCK 304), then processing proceeds to block 306, at which the surgeon console 170 continues to operate in normal mode. If the surgeon console 170 determines that the user is disengaged with the surgeon console 170 ("DISENGAGED" AT BLOCK 304), then processing proceeds to block 308, at which the surgeon console 170 ceases to operate in the normal mode and begins to operate in a safe mode (such as the safe modes described below). From each of steps 306 and 308, processing proceeds to step 316, which is described below.

Referring back to step 302, if the surgeon console 170 determines that the surgeon console 170 is currently operating in a safe mode ("SAFE MODE" at step 302) then processing proceeds to block 310. At block 310, the surgeon console 170 determines whether the user is engaged with, or disengaged from, the surgeon console 170. Exemplary aspects of how the surgeon console 170 makes the determination at step 304 are provided below in connection with FIG. 4 and FIG. 5. If the surgeon console 170 determines that the user is disengaged with the surgeon console 170 ("DISENGAGED" AT BLOCK 310), then processing proceeds to block 312, at which the surgeon console 170 continues to operate in the safe mode. If the surgeon console 170 determines that the user is engaged with the surgeon console 170 ("ENGAGED" AT BLOCK 310), then processing proceeds to block 314, at which the surgeon console 170 ceases to operate in the safe mode and begins to operate in the normal mode. From each of steps 312 and 314, processing proceeds to step 316.

At step 316, the surgeon console 170 determines whether to terminate the operation of the surgeon console 170, for example, by determining whether a user has inputted a command to shut down the surgeon console 170. If the surgeon console 170 determines that operation of the surgeon console 170 is to be terminated ("YES" at 316), then the surgeon console 170 enters an inactive state (for example, a powered down state or a sleep state) and the method 300 is terminated. If the surgeon console 170 determines that operation of the surgeon console 170 is not to be terminated ("NO" at 316), then processing proceeds back to step 302 as described above.

Figure 4:
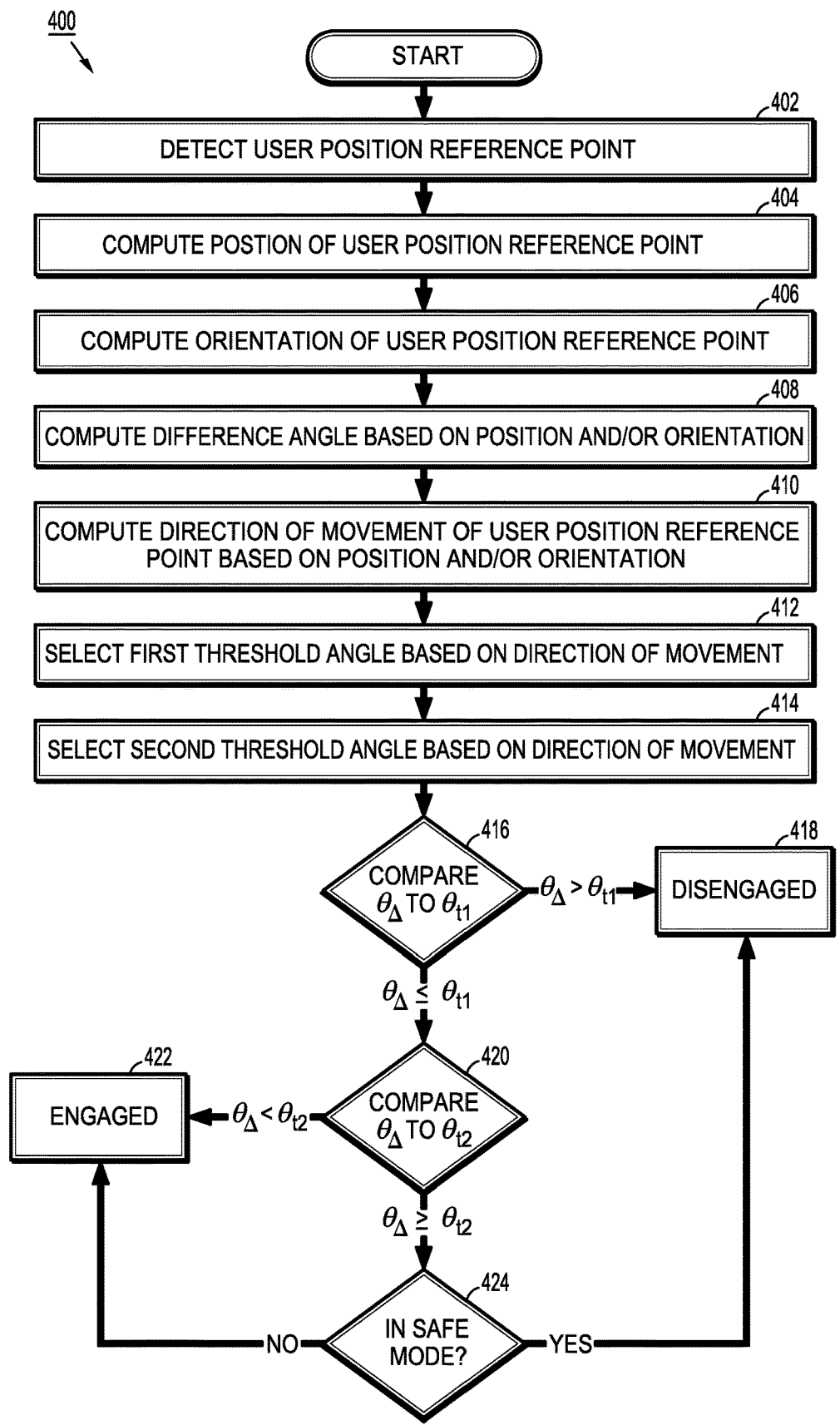
FIG. 4 is a flowchart that illustrates an exemplary method for determining whether a user is engaged with, or disengaged from, a surgeon console of the robotic surgical system of FIG. 1.

FIG. 4 is a flowchart that illustrates an exemplary method for determining whether a user is engaged with, or disengaged from, the surgeon console 170 of the robotic surgical system 100 of FIG. 1. At step 402, the surgeon console 170 detects a user position reference point in one of a variety of ways. For example, in an embodiment where the user position reference point is a portion of the user (such as a head, an eye, and/or the like), the surgeon console 170 may detect the user position reference point by capturing via the image capture device 161 an image including the portion of the user and by executing one or more known image recognition algorithms on the captured image. In an embodiment where the user position reference point is a portion of eyewear 163 worn by the user (such as one or more user position reference points corresponding to three of the markers 164), the surgeon console 170 may detect the user position reference point by capturing via the image capture device 161 an image including the markers 164, and by executing one or more image recognition algorithms on the captured image.

At step 404, the surgeon console 170 computes a position of the detected user position reference point relative to the display device 122. In step 406, the surgeon console 170 computes an orientation of the detected user position reference point relative to the display device 122. In embodiments where the image capture device 161 is equipped with an IR pass filter and IR LEDs and the surgeon console 170 is configured to perform optical tracking, the surgeon console 170 computes the position and orientation of one or more markers relative to the display device 122 and, based on the position and orientation of the one or more markers, computes the position and orientation of the user position reference point and/or of a portion of the user.

In step 408, the surgeon console 170 computes a difference angle $\theta_A$ 201 based on the position and orientation of the user position reference point that were computed at steps 404 and 406, respectively. As described above, in computing the difference angle $\theta_A$ 201, the surgeon console 170 computes a position of an imaginary line normal to a plane defined by the user position reference point and a position of the imaginary line normal to the front plane of the display device 122, and computes an angle $\theta_A$ 201 between the positions as the difference angle. In step 410, the surgeon console 170 computes a direction of movement of the user position reference point based on the position and the orientation of the user position reference point that were computed at steps 404 and 406, respectively. In some embodiments, the surgeon console 170 computes the direction of movement of the user position reference point by comparing the position and orientation of the user position reference point in a current time instance with the position and orientation of a prior time instance.

In step 412, the surgeon console 170 selects a first threshold angle $\theta_{t1}$ (for example, with reference to FIG. 2B and FIG. 2C, $\theta_{t1u}$ 202 for the upward direction or $\theta_{t1d}$ 204 for the downward direction) based on the direction of the movement of the portion of the user. Each possible direction of movement of the user position reference point, or at least a subset of the possible directions of movement of the user position reference point, is associated with a threshold angle, and the association between a threshold angle and the direction of the movement of the user position reference point is specified in a set of rules stored in a memory unit of the surgeon console 170, such as one of the memory units 134, or in a storage device operably coupled to the surgeon console 170. For example, if each cardinal direction of movement, such as up, down, left, right, are associated with a first threshold angle, then the set of rules specify a corresponding first threshold angle $\theta_{t1}$ for each of up, down, left, and right, and the surgeon console 170, using the set of rules, selects a first threshold angle corresponding to the computed direction of movement of the user position reference point.

In some embodiments, a threshold angle associated with one direction of movement is of a different size than a threshold angle associated with another direction of movement. For example, a threshold angle associated with the down direction of movement (for instance, with reference to FIG. 2C, $\theta_{t1d}$ 204) may be larger than the threshold angle associated with the right direction of movement (not shown in FIG. 2C). The size of a threshold angle for a particular direction of movement is based in part on whether a component of the surgical system 100 is positioned in that direction and the distance of that component from the display device 122. For example, if the foot pedal 128 is positioned below the display device 122 then the size of the threshold angle for the down direction should be large enough to accommodate the user looking at the foot pedal 128 without identifying that user as a user that is disengaged from the surgeon console 170. In some embodiments, the size of a threshold angle for a particular direction of movement depends upon the likelihood the user of the surgeon console 170 interacts with the component of the surgical system 100 in that direction. For example, if a second display device is positioned to the right of the display device 122, but the second display device does not provide any useful information to the user of the surgeon console 170, then it is unlikely that the user will look at the second display device while still intending to be engaged with the surgeon console 170. Thus the threshold angle associated with the direction in which the second display device is positioned, the right direction in this example, should not be large enough to accommodate the user looking at the second display device. However, if the second display device provides useful information to the user or with which the user interacts, then it is more likely that the user will look at the second display device and the size of the threshold angle in that direction should be large enough to accommodate the user looking at the second display device.

In some embodiments, the surgeon console 170 is configured to identify, relative to a user facing the display device 122, the position and orientation of an additional component that is operably and communicatively coupled to the surgeon console 170 and increase the threshold angle associated with that direction based on the position and the orientation of the additional component. For example, if a display device, additional to the default number of display devices, is operably and communicatively coupled to the surgeon console 170 to the right side of a user facing the surgeon console 170, then the surgeon console 170 increases the threshold angle associated with the right direction of the user based on the position and orientation of the additional display device relative to the user facing the display device 122 or using the surgeon console 170. In some embodiments, the position and orientation of an additional component that is operably and communicatively coupled to the surgeon console 170 is provided to the surgeon console 170 as an input, and the surgeon console 170 determines the direction, relative to the user of the surgeon console 170, in which the additional component is located, computes an increase in the size of the threshold angle associated with that direction, and increases that threshold angle by that computed increase in size.

Thus, by specifying different threshold angles for different direction of movements, the surgeon console 170 reduces the possibility of falsely identifying a user as being disengaged from the surgeon console 170 when the user is engaged with the surgeon console 170. Reducing such false identifications, further reduces falsely causing the surgical system 100 to initiate and operate in a safe mode and improves overall efficiency of the surgical system 100.

In some embodiments, each direction of movement is also associated with a second threshold angle $\theta_{t2}$ (for example, with reference to FIG. 2B and FIG. 2C, $\theta_{t2u}$ 203 for the upward direction or $\theta_{t2d}$ 205 for the downward direction), smaller than the first threshold angle $\theta_{t1}$ (for example, $\theta_{t1u}$ 202 for the upward direction or $\theta_{t1d}$ 204 for the downward direction), and the set of rules specifies the associated second threshold angle $\theta_{t2}$ for each direction of movement. In such embodiments, in step 414, the surgeon console 170, using the set of rules, selects a second threshold angle $\theta_{t2}$ corresponding to the direction of movement of the user position reference point computed at step 410. The second threshold angle $\theta_{t2}$ is used to determine whether a user, who has been identified as being disengaged from the surgeon console 170, is re-engaged with the surgeon console 170. By providing a second threshold angle $\theta_{t2}$ smaller than the first threshold angle $\theta_{t1}$, the surgical system 100 creates a buffer that prevents the surgical system 100 from quickly oscillating between operating in a safe mode and non-safe mode.

In step 416, the surgeon console 170 compares the difference angle $\theta_A$ 201, which was computed at step 408 based on the position and the orientation of the user position reference point computed at steps 404 and 406, respectively, is greater than the first threshold angle $\theta_{t1}$. If the surgeon console 170 determines that the difference angle $\theta_A$ 201 is greater than the first threshold angle $\theta_{t1}$ ("$\theta_A > \theta_{t1}$" at step 416), then, in step 418, the surgeon console 170 determines that the user is disengaged. In some embodiments, as described above in connection with steps 308 and/or 312 of FIG. 3, the surgeon console 170, in response to identifying the user as being disengaged, causes the surgical system 100 to operate in a selected safe mode, for instance, by initiating and processing steps associated with the selected safe mode.

In some embodiments, the surgeon console 170 is configured with an indicator, stored in a memory unit 134 or in a storage device operably coupled to the surgeon console 170, the value of which indicates whether the surgical system 100 is operating in a safe mode or a non-safe mode, referred to herein as "safe mode indicator," and the surgeon console 170 determines whether the surgical system 100 is operating in a safe mode based at least in part on the value of the safe mode indicator. The surgeon console 170 is configured to update the value of the safe mode indicator to indicate that the surgical system 100 is operating in a safe mode at a time when the surgical system 100 is caused to operate in a safe mode or at a time when the user is identified as being disengaged from the surgeon console 170. Examples of a safe mode indicator include, but are not limited to, a flag variable, the value of which the surgeon console 170 updates to indicate whether the surgical system 100 is operating in a safe mode, for example by setting the value of the flag variable to a one (1) to indicate that the surgical system 100 is operating in a safe mode and to a zero (0) to indicate that the surgical system 100 is operating in a non-safe mode.

In some embodiments, the surgeon console 170 is configured to select a default safe mode specified in a set of rules stored in a memory unit of the surgeon console 170, such as memory units 134 or storage device operably coupled to the surgeon console 170. In some embodiments, a list of multiple safe modes, each of which is associated with a ranking, is stored in one or more memory units 134 or a storage device operably coupled to the surgeon console 170, and the surgeon console 170 is configured to select from the list of multiple safe modes based on the ranking associated with the safe modes. In some embodiments, the surgeon console 170 provides a GUI presenting a list of various safe modes in which the surgical system 100 is configured to operate and the user selects a safe mode and provides the selection as an input to the surgeon console 170 using the GUI. Additional details of some of the safe modes in which the surgical system 100 is configured to operate are provided herein in the contexts of FIG. 6 and FIG. 7.

In step 416, if the surgeon console 170 determines that the difference angle $\theta_A$ 201 is not greater than the first threshold angle $\theta_{t1}$ ("$\theta_A \leq \theta_{t1}$" at step 416), then, in embodiments where a second threshold angle $\theta_{t2}$ is associated with a direction of movement and the second threshold angle $\theta_{t2}$ is selected, the surgeon console 170 proceeds to step 420. In step 420, the surgeon console 170 compares the difference angle $\theta_A$ to the second threshold angle $\theta_{t2}$. If the surgeon console determines that the difference angle $\theta_A$ is less than the second threshold angle $\theta_{t2}$ ("$\theta_A < \theta_{t2}$" at step 420), then, in step 422, the surgeon console 170 determines that the user is engaged. In embodiments, the surgeon console 170 may further determine an XYZ position of the user (that is, determine a position of the user's head, face, or 3D glasses in three-dimensional space relative to the surgeon console 170) to determine whether the user is engaged. For example, by determining the XYZ position of the user relative to the surgeon console 170, the surgeon console 170 can determine whether the user is too far away from the surgeon console and provide a notification indicating such. Additionally, in embodiments where multiple individuals are within a predetermined distance of the surgeon console 170, the surgeon console 170 can ensure that the correct individual (i.e. the user) is tracked and that another individual standing behind the user is not determined as engaged with the surgeon console 170.

If the surgeon console 170 determines that the difference angle $\theta_A$ is not less than the second threshold angle $\theta_{t2}$ ("$\theta_A \geq \theta_{t2}$" at step 420), then, at step 424, the surgeon console 170 determines whether the surgical system 100 is operating in a safe mode. In some embodiments, the surgeon console 170 may additionally determine whether a displacement of the user is larger than a predetermined threshold. Additionally or alternatively, the surgeon console 170 may determine a displacement gradient. By determining the displacement gradient and/or whether the displacement is larger than a predetermined threshold, the surgeon console 170 may determine if a displacement is too large over too short a period of time, as may be the case if there are multiple individuals in an engagement zone of the surgeon console 170 and movement of an individual other than the user is mistakenly attributed to the user or the tracker jumps from one user to another. If it is determined that the displacement is larger than the predetermined threshold or the displacement gradient indicates that the tracker may have jumped between individuals, the safe mode may be activated. If the surgeon console 170 determines that the surgical system 100 is operating in a safe mode ("YES" at step 424), then, in step 418, the surgeon console 170 identifies the user as disengaged with the surgeon console 170. If the surgeon console 170 determines that the surgical system 100 is not operating in a safe mode ("NO" at step 424), then, in step 422, the surgeon console 170 identifies the user as being engaged (or re-engaged, as the case may be) with the surgeon console 170. As described above in connection with steps 306 and/or 314 of FIG. 3, the surgeon console 170, in response to identifying the user as being engaged, causes the surgical system 100 to operate in a normal (non-safe) mode, for instance, by initiating and processing steps associated with the normal mode. In some embodiments, in step 420, the surgeon console 170 is configured to wait for a threshold amount of time prior to identifying the user as being re-engaged with the surgeon console 170. In embodiments where the surgeon console 170 is configured with a safe mode indicator, the surgeon console 170 updates the value of the safe mode indicator to indicate that the surgical system 100 is not operating in a safe mode at time when the user is identified as re-engaged or engaged with the surgeon console 170 or at a time when the surgical system 100 is caused to exit the safe mode.

Figure 5:
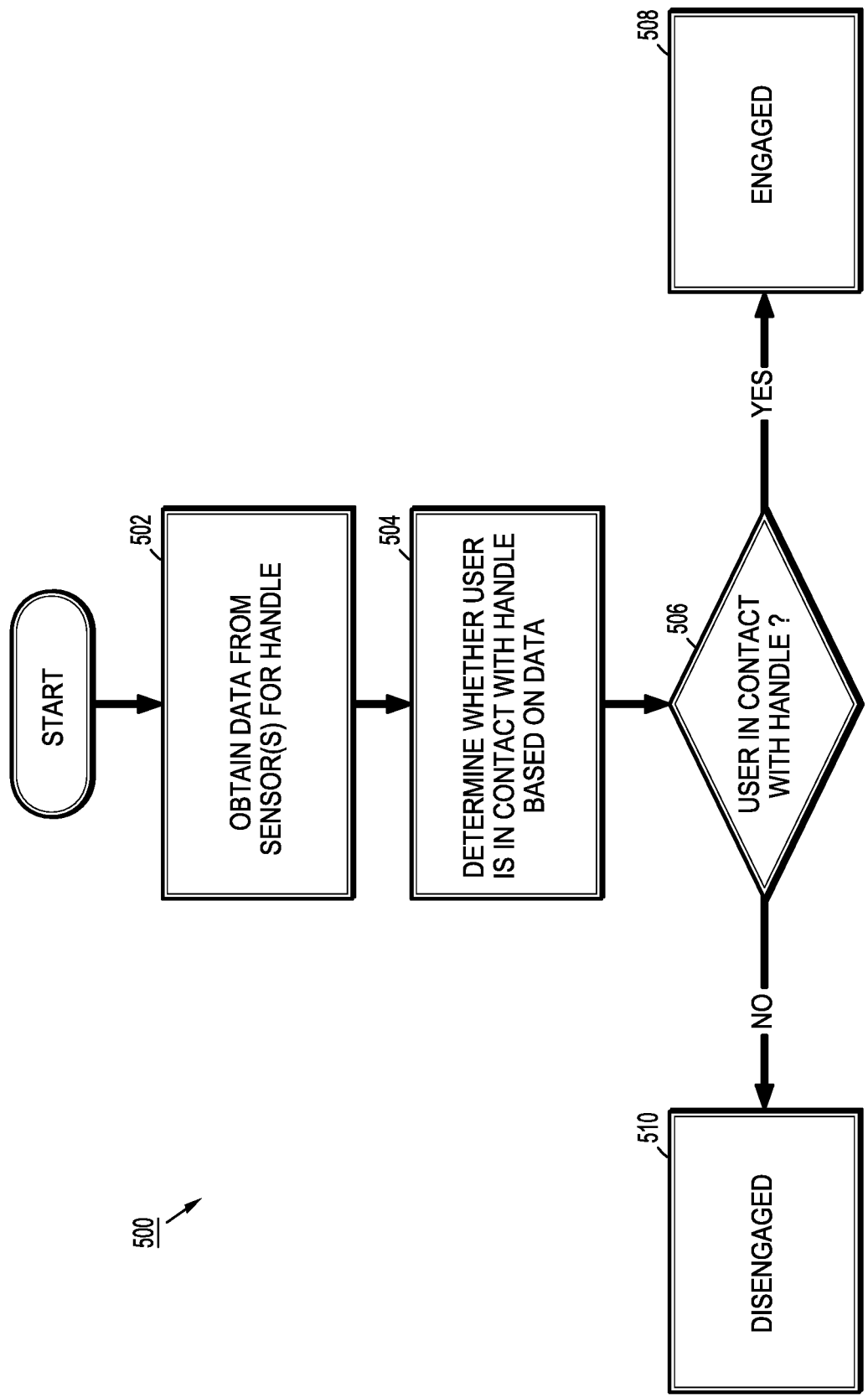
FIG. 5 is a flowchart that illustrates another exemplary method for determining whether a user is engaged with, or disengaged from, a surgeon console of the robotic surgical system of FIG. 1.
Figure 6:
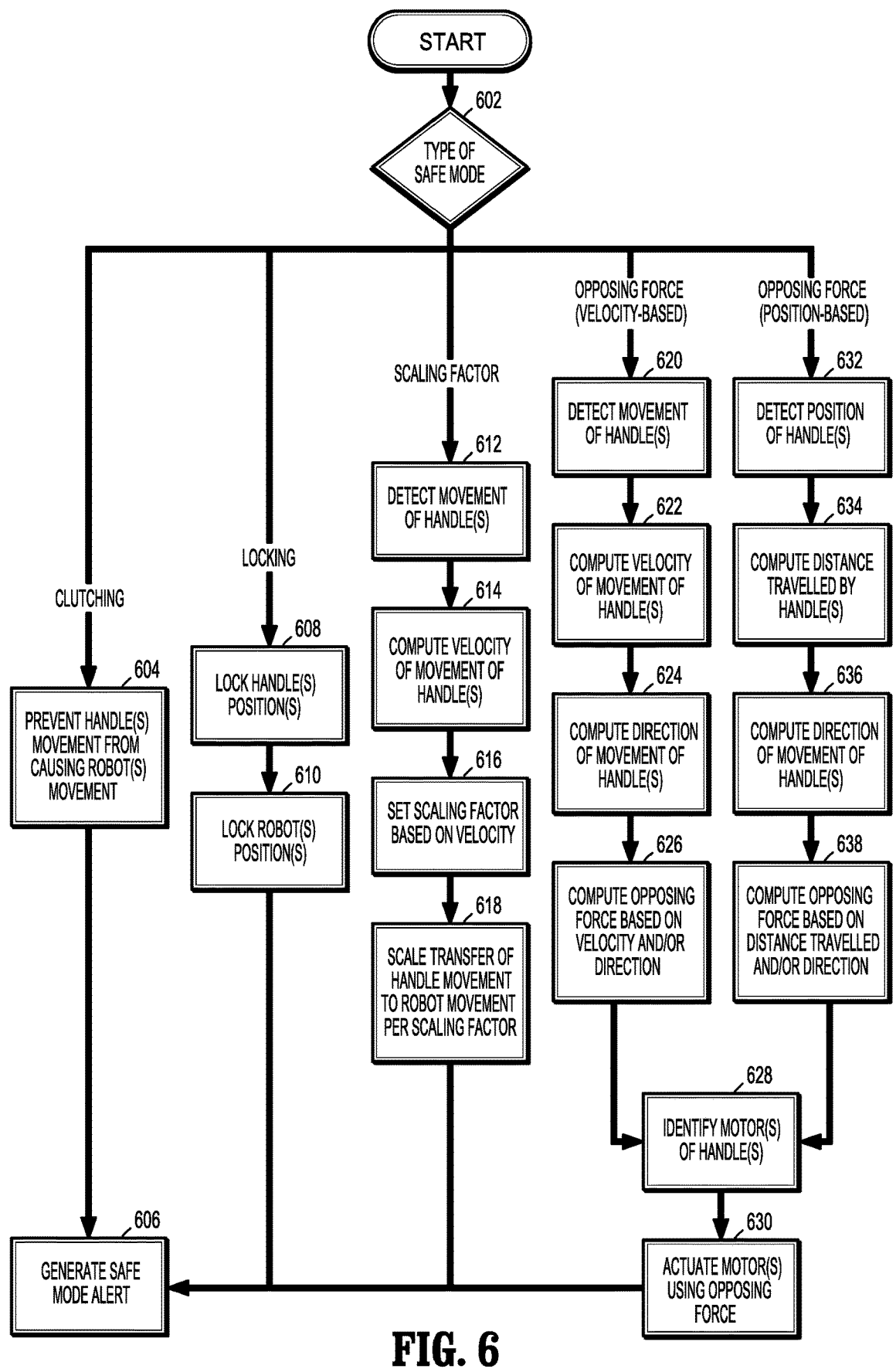
FIG. 6 is a flowchart that illustrates an exemplary method for operating the robotic surgical system of FIG. 1 in one or more safe modes of operation.

FIG. 5 shows another illustrative method 500 of determining whether the user of the surgeon console 170 is engaged or disengaged from the surgeon console 170. In various embodiments, the surgeon console 170 may be configured to determine whether the user is engaged with, or disengaged from, the surgeon console 170 by employing the method 300 (FIG. 3) and/or the method 400 (FIG. 4) either individually or in any combination with one another.

At step 502, processor 133 of the surgeon console 170 obtains data from one or more sensor(s) 130 indicating whether the user is in contact with one or more handles 112 of the surgeon console 170. At step 504, the surgeon console 170 determines whether the user is in contact with the handles 112 based on the data obtained at step 502. In particular, for instance, the surgeon console 170 may determine at step 504 whether the user is in contact with a handle 112A based on outputs from one or more sensors 130A, such as capacitive and/or optical sensors, that are coupled to the handle 112A and configured to identify the user's contact with the handle 112A. Exemplary types of outputs from such sensor 130A include, but are not limited to, a high signal or a one (1) when a user is in contact with a handle 112A coupled to the sensors and a low signal or a zero (0) when the user is not in contact with the handle 112A. For example, the sensor 130A is a capacitive sensor configured to transmit a high signal or a one (1) to the processor 133 of the surgeon console 170 when the user is in contact with the handle 112A and a low signal or a zero (0) when the user is not in contact with the handle 112A, then the surgeon console 170 determines that the user is in contact with the handle 112A if a high signal or a 1 is received by the processor 133 from the capacitive sensor 130A and that the user is not in contact with the handle 112A if a low signal or a zero (0) is received by the processor 133 from the capacitive sensor 130A. In some embodiments, the surgeon console 170 determines that the user is in contact with the surgeon console 170 if the user is simultaneously in contact with a majority of the handles 112. For example, if the surgeon console 170 includes three handles 112 and the surgeon console is configured to determine that a user is in contact with the surgeon console 170 if the user is contact with a majority of the handles 112, then the surgeon console 170 determines that the user is in contact with the surgeon console 170 if the user is simultaneously in contact with at least two of the handles 112. Similarly, if the surgeon console 170 includes two handles 112, then the surgeon console 170 determines that the user is in contact with the surgeon console 170 if the user is in contact with both of the handles 112, a majority of the handles 112 of the surgeon console 170.

In step 506, if the surgeon console 170 determines that the user is not in contact with the surgeon console 170 ("NO" at step 506), then, in step 510, the surgeon console 170 identifies the user as disengaged from the surgeon console 170. In step 506, if the surgeon console 170 determines that the user is in contact with the surgeon console 170 ("YES" at step 506), then, in step 508, the surgeon console 170 identifies the user as re-engaged with the surgeon console 170.

Figure 7:
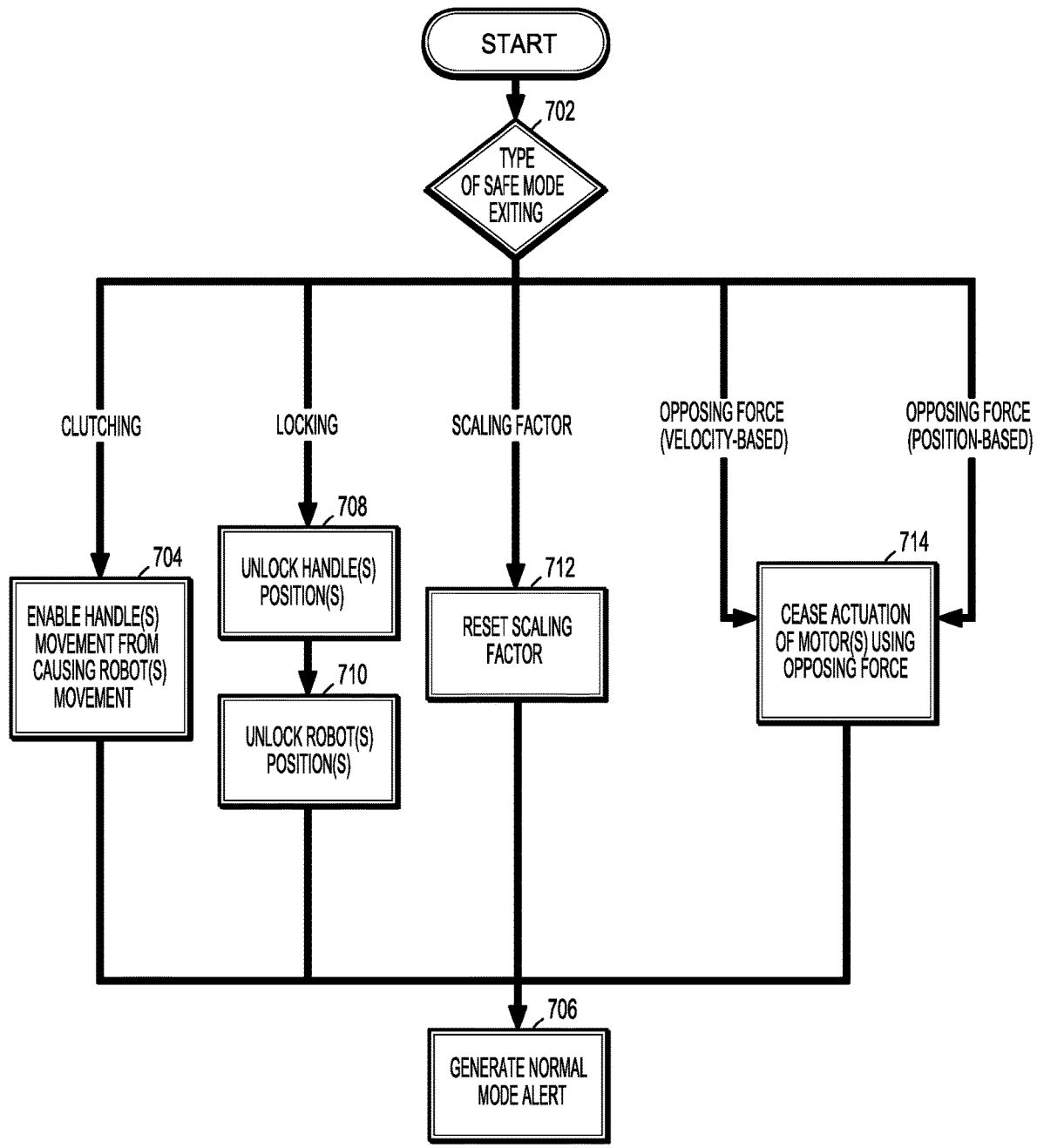
FIG. 7 is a flowchart that illustrates an exemplary method for terminating one or more safe modes of operation of the robotic surgical system of FIG. 1.

As described above, the surgical system 100 is configured to operate in one or more safe modes, either individually or in any combination, and additional details of these safe modes are provided herein in the contexts of FIG. 6 and FIG. 7. In particular, FIG. 6 and FIG. 7 shows a flowchart that illustrates an exemplary method 600 for operating the robotic surgical system 100 of FIG. 1 in one or more of the following five illustrative safe modes of operation: (1) a clutching safe mode, (2) a locking safe mode, (3) a scaling factor safe mode, (4) an opposing force safe mode based on handle velocity, and (5) an opposing force safe mode based on handle position. In some embodiments, the surgical system 100 is configured to enter (see, for example, step 308 of FIG. 3) or remain in (see, for example, step 312 of FIG. 3) one or more of the safe modes according to the method 600, based on a determination (see, for example, steps 304 and/or 310 of FIG. 3, method 400 of FIG. 4, and/or method 500 of FIG. 5) as to whether the user is engaged with, or disengaged from, the surgeon console 170. Referring now to FIG. 6, at step 602, the surgeon console 170 determines which safe mode to enter or remain in, for instance, based on a value of the safe mode indicator described above.

Although some safe modes are described herein in the context of controlling one of the robot assemblies 190 or subunits 191, 192, 193, and 194 thereof, in various embodiments, safe modes include simultaneously controlling multiple robot assemblies 190 and/or the subunits 191, 192, 193, and 194 thereof.

If the surgeon console 170 determines to enter or remain in the clutching safe mode ("CLUTCHING" at step 602), then processing proceeds to step 604. While the surgical system 100 is operating in a non-safe mode, the surgeon console 170 causes one or more of the subunits 191, 192, 193, and 194 of the robot of assemblies 190 to be moved by transmitting data related to the movement of the handles 112 of the surgeon console 170 to one or more of the subunits 191, 192, 193, and 194 of the robot assemblies 190 that are communicatively coupled to the handles 112, and one or more of the subunits 191, 192, 193, 194 that receives data related to the movement of the handles 112 moves based in part on the received data.

In step 604, while the surgical system 100 operates in the clutching safe mode, for each handle 112 of the surgeon console 170, the surgeon console 170 prevents movement of the handle 112 from causing a corresponding movement of the one or more of the subunits 191, 192, 193, and 194 of the robot assembly 190 communicatively coupled to that handle 112, for instance, by preventing the transmission of data related to the movement of the handle 112 to the subunit(s) 191, 192, 193, and/or 194. In some embodiments, the surgeon console 170 is configured with an indicator, stored in a memory unit 134 or in a storage device operably coupled to the surgeon console 170, the value of which indicates whether the clutching safe mode is enabled or disabled, referred to herein as "clutching safe mode indicator," and the surgeon console 170 determines whether to transmit data related to the movement of the handles 112 based in part on the values of the movement translation indicator. Examples of values of the clutching safe mode indicator that indicate that clutching safe mode is disenabled is a one (1) or a sequence of ones (e.g. "11111"), and the examples of values of the clutching safe mode indicator that indicate that the clutching safe mode is enabled is a zero (0) or a sequence of zeroes (e.g. "00000"). In some embodiments, each bit of the value of the clutching safe mode indicator is associated with a handle 112 of the surgeon console 170, and the surgeon console 170 determines whether to transmit movement data of a particular handle 112 based in part on the value of the bit associated with that handle 112. For example, the zero$^{th}$ bit of the value may be associated with the handle 112A and the first bit of the value may be associated with the handle 112B, and the surgeon console 170 determines whether to transmit data related to the movement of the handle 112A based on whether the zero$^{th}$ bit is high (1) or low (0), and the surgeon console 170 determines whether to transmit data related to the movement of the handle 112B based on whether the first bit is high or low.

The surgeon console 170 is configured to update the value of the clutching safe mode indicator to indicate that the clutching safe mode is enabled at a time when translation of movement from the movement of the handle 112 to the movement of the communicatively coupled robot arm is disabled. From step 604, processing proceeds to step 606, at which the surgeon console 170 provides an alert to the user that indicates that the surgeon console 170 is in a safe mode (in this case, the clutching safe mode. Examples of the alerts that may be provided at step 606 include, but are not limited to, visual and/or auditory alerts, similar to the alerts described above.

Referring back to step 602, if the surgeon console 170 determines to enter or remain in the locking safe mode ("LOCKING" at step 602), then processing proceeds to step 608. At step 608, the surgeon console 170 locks each handle 112 of the surgeon console 170 in its position and prevents the movement of the handles 112 from their positions. In some embodiments, the surgeon console 170 identifies the position of each of the handles 112 at the time of locking the handles 112 and stores data related to the positions of the handles 112 in a memory unit 134 of the surgeon console 170 or a storage device operably coupled to the surgeon console 170. In some embodiments, the surgeon console 170 locks the handles 112 in their position by preventing movement of the motors and actuators of the handles 112, such as motors 132A and 132B. For example, the surgeon console 170 may cause the motors to servo or apply torque to restore the handles 112 to the stored position such that each subunit 191, 192, 193, 194 that is locked maintains the stored position. In step 610, the surgeon console 170 causes each of the subunits 191, 192, 193, 194 that are communicatively coupled to the handles 112 to be locked in its position by transmitting a lock instruction to each of the subunits 191, 192, 193, 194. As described above, the surgeon console 170 is communicatively coupled to the robot assemblies 190, via the computing device 180 and the surgeon console 170 transmits instructions to lock the subunits 191, 192, 193, 194 to the robot assemblies 190 by transmitting the instructions to the computing device 180, which in turn transmits the instructions to the robot assemblies 190. In some embodiments, the surgeon console 170 is directly communicatively coupled to each robot assembly 190 of the surgical system 100 and the surgeon console 170 transmits instructions to lock the robot arms in their positions directly to the robot assemblies 190 of the robot arms communicatively coupled to the handles 112. Each robot assembly that receives the instructions, locks its robot arm in its position in response to receiving the instructions.

From step 610, processing proceeds to step 606, at which the surgeon console 170 provides an alert to the user that indicates that a safe mode (the locking safe mode, in this instance) is activated. In some embodiments, the surgeon console 170 provides a visual alert indicating that the handles 112 and the communicatively coupled robot arms are locked. An example of the visual alert includes, but is not limited to, a graphical item displayed on one or more display devices of the surgeon console 170, such as the display device 122. Another example of the visual alert includes a light emitting diode (LED) on the surgeon console 170 that is powered on at the time the handles 112 and the communicatively coupled robot arms are locked. In some embodiments, the surgeon console 170 is configured to provide an auditory alert, such as a sound recording, and/or a tactile alert such as vibration or other physical feedback that indicates that the handles 112 and the communicatively coupled robot arms are locked.

Referring back to step 602, if the surgeon console 170 determines to enter or remain in a scaling factor safe mode ("SCALING FACTOR" at step 602), then processing proceeds to step 612. At step 612, the surgeon console 170 detects movement of the handle 112 of the surgeon console 170. As described above, each handle 112 is operably and communicatively coupled to one or more sensors 130 that are configured to detect movement of the handle 112 and the velocity of the movement of the handle 112 and output values that indicate whether the handle 112 is moved and/or the velocity of the handle 112. Based on the output values of the one or more sensors 130 coupled to the handle 112, the surgeon console 170 detects movement of the handle 112. At step 614, the surgeon console 170 computes a velocity at which the handle 112 is moved. As described above, the surgeon console 170 computes the velocity based on based on multiple positions of the handle sensed over time via the one or more sensors 130 coupled to the handle 112 and configured to sense movement of the handle 112.

At step 616, the surgeon console 170, based on the velocity of the movement of the handle 112 computed at step 614, selects a scaling factor from a list of safe-mode scaling factors. As used herein, the term "scaling factor" refers to a ratio between a movement of a handle 112 to a corresponding movement that is caused of one or more subunits 191, 192, 193, and 194 communicatively coupled to the handle 112. For example, a scaling factor of 3:1 indicates that a movement of the handle 112 by three inches translates to a movement of the communicatively coupled subunit 191, 192, 193, and/or 194 by 1 inch. Similarly, a scaling factor of 50:1 indicates that movement of the handle 112 by 5 inches translates to a movement of the communicatively coupled subunit 191, 192, 193, and/or 194 by 0.1 inch. A safe mode scaling factor is a scaling factor specified in a set of rules or configuration data, which the surgeon console 170 is configured to use if the surgical system 100 is operating in a scaling factor safe mode. The set of rules or configuration data further specify a velocity or a range of velocities for each safe mode scaling factor, and are stored in one or more memory units of the memory units 134 or a storage device operably coupled to the surgeon console 170. In some embodiments, in selecting a scaling factor from the list of safe mode scaling factors, the surgeon console 170 identifies the velocity that is closest to the computed velocity of the handle 112 or the range of velocities which includes the computed velocity, and selects the associated scaling factor. In other embodiments, the surgeon console 170 computes a velocity of a movement of the handle 112 and modifies the downward scaling factor based on the computed velocity.

At step 618, the surgeon console 170 applies the safe mode scaling factor selected at step 616 to the distance travelled by the handle 112 to compute the scaled distance, and transmits the scaled distance to one or more of the subunits 191, 192, 193, or 194 communicatively coupled to the handle 112, which move based in part on the received scaled distance. The selected safe mode scaling factor may, in some examples, be a downward scaling factor that, relative to a non-safe mode scaling factor, causes a small amount of movement of one or more of the subunits 191, 192, 193, or 194 for a given amount of movement of the handle 112. In some embodiments, the surgeon console 170 transmits the selected safe-mode scaling factor and the distance travelled by the handle 112 to a particular one or more of the subunits, 191, 192, 193, and/or 194, and the scaled distance is computed based in part upon which the robot arm is moved. After step 710, the surgeon console 170 returns to step 302 (shown in FIG. 3A). From step 618, processing proceeds to step 606, at which the surgeon console 170 provides a visual and/or an auditory alert to the user indicating that the safe mode based on handle velocity is enabled.

Referring again to step 602, if the surgeon console 170 determines to enter or remain in the opposing force safe mode based on handle velocity ("OPPOSING FORCE (VELOCITY-BASED)" at step 602), then processing proceeds to step 620. At step 620, the surgeon detects movement of one or more of the handles 112. The surgeon console 170 detects movement of the handles 112 in a similar manner as described above for step 612. At step 622, the surgeon console 170 computes the velocity of the movement of the handle 112 using the one or more sensors 130 that are operably and communicatively coupled to the handle 112.

At step 624, the surgeon console 170 computes a direction of the movement of the handle 112. As described above, one or more of the sensors 130 are configured to sense a direction of movement of the handle 112 in one or more directions, and the surgeon console 170 computes the direction of the movement of the handle 112, for example relative to a prior position of the handle 112, based on the outputs from the one or more sensors 130.

In step 626, the surgeon console 170, based on the computed velocity of the movement of the handle 112 and the computed direction of the movement of the handle 112, computes an opposing force to be applied to the handle 112 in a direction opposite to the computed direction of movement of the handle 112. At step 628, the surgeon console 170 identifies a motor, among the motors 132 of the handle 112, associated with the direction in which the opposing force computed at 626 is to be applied, and, at step 630, the surgeon console 170 actuates the identified motor in the direction opposite to the computed direction of movement of the handle 112 at a speed sufficient to generate the opposing force computed at step 626 in the direction opposite to the computed direction of handle movement and thereby significantly reduce any travel of the handle 112. Thus, the surgeon console 170 provides sufficient force to the user in the direction opposite to the direction of movement of handle 112, thereby providing a haptic feedback to the user that the surgical system 100 is operating in a safe mode. From step 630, processing proceeds to step 606 to provide an alert that the safe mode (the opposing force safe mode based on velocity, in this instance) is activated.

Referring again to step 602, if the surgeon console 170 determines to enter or remain in the opposing force safe mode based on handle position ("OPPOSING FORCE (POSITION-BASED)" at step 602), then processing proceeds to step 632. At step 632, for each handle 112, the surgeon console 170 identifies the position of the handle 112 at the time the surgical system 100 is caused to operate in the opposing force safe mode based on handle position. The surgeon console 170 stores the identified position of the handle 112 in a memory unit 134 or a data storage device operably coupled to the surgeon console 170.

At step 634, the surgeon console 170 detects movement of one or more of the handles 112 from its respective position identified at step 632. At step 634, the surgeon console 170 computes a distance traveled by the handle(s) 112 that moved. As described above, one or more sensors 130 coupled to the handles 112 is configured to sense a distance the handle 112 travels and the surgeon console 170 computes the distance traveled by the handles 112 using the data from the one or more sensors 130.

At step 636, the surgeon console 170 computes a direction of the movement of the handle 112 and, at step 638, based on the computed velocity of the movement of the handle 112 and/or the computed direction of the movement of the handle 112, the surgeon console 170 computes an opposing force to be applied to the handle 112 in a direction opposite to the computed direction of handle movement. At step 628, the surgeon console 170 identifies a motor, among the motors 132 of the handle 112, associated with the computed direction of movement, and, at step 630, the surgeon console 170 rotates the identified motor at a speed sufficient to generate the computed opposing force in the direction opposite to the computed handle movement direction, and continues to actuate the motor until the handle 112 returns to the position identified at step 632, thereby reducing any travel of the handle 112 and providing feedback to the user indicating that the motion is being resisted, thereby alerting the user that the surgical system 100 is operating in a safe mode.

FIG. 7 is a flowchart that illustrates an exemplary method 700 for terminating one or more safe modes of operation of the robotic surgical system 100 of FIG. 1. At step 702, the surgeon console 170 determines which safe mode to exit, for instance, based on a value of the safe mode indicator described above. If the surgeon console 170 determines to exit the clutching safe mode ("CLUTCHING" at step 702) then processing proceeds to step 704. At step 704, for each handle 112 of the surgeon console 170, the surgeon console 170 enables the translation of movement from the movement of the handle 112 to the movement of the subunit 191, 192, 193, and/or 194 communicatively coupled to the handle 112 by enabling the transmission of data related to the movement of the handle 112 to the subunit(s) 191, 192, 193, or 194. In embodiments where the surgeon console 170 is configured with a clutching safe mode indicator, the surgeon console 170 updates the value of the clutching safe mode indicator to a value that indicates that the clutching safe mode is disabled. At step 706, the surgeon console 170 provides an alert to the user that indicates that the clutching safe mode is disabled and/or that the normal (non-safe) mode is enabled.

If the surgeon console 170 determines to exit the locking safe mode ("LOCKING" at step 702) then processing proceeds to step 708. At step 708, the surgeon console 170 unlocks each handle 112 of the surgeon console 170. In some embodiments, the surgeon console 170 unlocks each handle 112 by actuating the motors 132 associated with the handle 112 as per their non-safe mode configuration in response to the user moving the handle 112. For example, the surgeon console 170 may unlock each handle 112 when it is determined that the surgeon is re-engaged (e.g. looking at the surgeon console 170), and/or after the user performs a predetermined action, such as actuating a button or pedal or performing a particular motion of the handle 112. At step 710, the surgeon console 170 causes each subunit 191, 192, 193, or 194 communicatively coupled to the handles 112 to be unlocked by, for example, transmitting to the computing device 180 instructions to unlock the subunit(s) 191, 192, 193, or 194, in response to which, the computing device 180 transmits the instructions to the subunit(s) 191, 192, 193, or 194. In embodiments where the robot assemblies 190 are directly connected to the surgeon console 170, the surgeon console 170 transmits the instructions to release the robot arms directly to the robot assemblies 190 of the robot arms communicatively coupled to the handles 112. Each robot assembly that receives the instructions, unlocks its subunit 191, 192, 193, and/or 194 in response to receiving the instructions.

At step 706, the surgeon console 170 provides an alert to the user that indicates that the safe mode has been exited and/or that the normal mode (non-safe mode) has been entered. In one example, the alert includes indicating that the handles 112 and the robot arms communicatively coupled to the handles 112 are unlocked. The alerts provided to the user, in some embodiments, are visual alerts and, in some embodiments, are auditory alerts. Examples of the visual alerts include, but are not limited to, graphical items displayed on one or more display devices of the surgeon console 170 and LEDs on the surgeon console 170.

Referring back to step 702, if the surgeon console 170 determines to exit the scaling factor safe mode ("SCALING FACTOR" at step 702) then processing proceeds to step 712. At step 712, the surgeon console 170 resets the scaling factor back to a predetermined value, such as a 1:1 value, to be used during normal (non-safe mode) operation.

If the surgeon console 170 determines to exit either the opposing force safe mode based on handle velocity or the opposing force safe mode based on handle position ("OPPOSING FORCE (VELOCITY BASED)" or "OPPOSING FORCE (POSITION-BASED)" at step 702) then processing proceeds to step 714. At step 714, the surgeon console 170 ceases actuation of the motors initiated at step 630 of FIG. 6. From step 714, processing proceeds to step 706, at which an alert is generated indicating that the safe mode has been disabled and the normal mode has been enabled.

The phrases "in an example," "in examples," "in some examples," "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory described herein. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A robotic surgical system with user engagement monitoring, comprising:
   a robot assembly including a robotic arm coupled to a surgical instrument;
   a surgeon console including:
      a handle communicatively coupled to at least one of the robot assembly, the robotic arm, or the surgical instrument, and
      a display device; and
   a tracking device including an image capture device configured to capture an image of a user position reference point,
   wherein at least one of the surgeon console or the tracking device is configured to:
      compute, based on the captured image, a position of the user position reference point relative to the display device,
      determine whether a user is engaged with or disengaged from the surgeon console based on the computed position, and
      in response to a determination that the user is disengaged from the surgeon console, cause the robotic surgical system to operate in a safe mode,
   wherein at least one of the surgeon console or the tracking device is further configured to compute the position of the user position reference point by generating location data corresponding to at least one of the position, or an orientation, of the user position reference point, within a three-dimensional coordinate space, relative to the display device;
   wherein, in the determination of whether the user is engaged with or disengaged from the surgeon console, at least one of the surgeon console or the tracking device is further configured to:
      compute a difference angle based on the position and orientation of the user position reference point relative to the display device;
      compare the difference angle to a first threshold angle;
      in response to a determination that the difference angle is greater than the first threshold angle, determine that the user is disengaged from the surgeon console;
      compute, based on the position and the orientation of the user position reference point, a direction of movement of the user position reference point relative to the display device; and
      select the first threshold angle based on the direction of movement of the user position reference point for use in commanding movement of the robot assembly.

2. The robotic surgical system of claim 1, wherein at least one of the surgeon console or the tracking device is further configured to select the first threshold angle from a plurality of first threshold angles based on the position and the orientation of the user position reference point relative to the display device.

3. The robotic surgical system of claim 1, wherein, in the determination of whether the user is engaged with or disengaged from the surgeon console, at least one of the surgeon console or the tracking device is further configured to:
in response to a determination that the difference angle is less than the first threshold angle, determine whether the difference angle is less than a second threshold angle that is smaller than the first threshold angle; and
in response to a determination that the difference angle is less than the second threshold angle, determine that the user is engaged with the surgeon console.

4. The robotic surgical system of claim 3, wherein at least one of the surgeon console or the tracking device is further configured to, in response to the determination that the user is engaged with the surgeon console, cause the robotic surgical system to exit the safe mode.

5. The robotic surgical system of claim 1, wherein at least one of the surgeon console or the tracking device is further configured to, at a time when the robotic surgical system operates in the safe mode:
in response to a determination that the user is engaged with the surgeon console, cause the robotic surgical system to exit the safe mode after an elapsing of a threshold amount of time after the determination that the user is engaged.

6. A robotic surgical system with user engagement monitoring, comprising:
a robot assembly including a robotic arm coupled to a surgical instrument;
a surgeon console including:
a handle communicatively coupled to at least one of the robot assembly, the robotic arm, or the surgical instrument, and
a display device; and
a tracking device including an image capture device configured to capture an image of a user position reference point,
wherein at least one of the surgeon console or the tracking device is configured to:
compute, based on the captured image, a position of the user position reference point relative to the display device,
determine whether a user is engaged with or disengaged from the surgeon console based on the computed position, and
in response to a determination that the user is disengaged from the surgeon console, cause the robotic surgical system to operate in a safe mode;
at a time when the robotic surgical system operates in the safe mode:
restrict movement of the handle from a previous position of the handle, and
transmit, to the computing device, instructions to restrict movement of at least one of the robot assembly, the robotic arm, or the surgical instrument;
wherein the computing device is configured to:
receive the instructions, and
transmit the instructions to at least one of the robot assembly, the robotic arm, or the surgical instrument; and
wherein at least one of the robotic arm, the robot assembly, or the surgical instrument is configured to:
receive the instructions, and
restrict movement of at least one of the robot assembly, the robotic arm, or the surgical instrument in response to the instructions.

7. The robotic surgical system of claim 1, wherein at least one of the surgeon console or the tracking device is further configured to, at a time when the robotic surgical system operates in the safe mode:
prevent a movement of the handle from causing a corresponding movement of the robotic arm communicatively coupled to the handle.

8. A robotic surgical system with user engagement monitoring, comprising:
a robot assembly including a robotic arm coupled to a surgical instrument;
a surgeon console including:
a handle communicatively coupled to at least one of the robot assembly, the robotic arm, or the surgical instrument, and
a display device; and
a tracking device including an image capture device configured to capture an image of a user position reference point,
wherein at least one of the surgeon console or the tracking device is configured to:
compute, based on the captured image, a position of the user position reference point relative to the display device,
determine whether a user is engaged with or disengaged from the surgeon console based on the computed position,
in response to a determination that the user is disengaged from the surgeon console, cause the robotic surgical system to operate in a safe mode;
detect an amount of movement of the handle;
determine, based on the amount of movement of the handle, an amount of movement of at least one of the robot assembly, the robotic arm, or the surgical instrument to be caused in response to the movement of the handle;
cause at least one of the robot assembly, the robotic arm, or the surgical instrument to move by the determined amount of movement,
wherein, at a time when the robotic surgical system operates in the safe mode, the determination of the amount of movement of at least one of the robot assembly, the robotic arm, or the surgical instrument to be caused includes applying a downward scaling factor.

9. The robotic surgical system of claim 8, wherein at least one of the surgeon console or the tracking device is further configured to:
compute a velocity of a movement of the handle; and
modify the downward scaling factor based on the velocity.

10. The robotic surgical system of claim 1, wherein the surgeon console includes a plurality of motors corresponding to the handle, each of the motors being operably coupled to the handle and being associated with a direction of movement of the handle,
wherein, at a time when the robotic surgical system operates in the safe mode, at least one of the surgeon console or the tracking device is further configured to:
compute a velocity of a movement of the handle,
compute a direction of the movement of the handle,
compute, based on the velocity of the movement of the handle, a force in a direction opposite to the direction of the movement of the handle, identify, among the plurality of motors of the handle, a motor associated with the direction opposite to the direction of the movement of the handle, and cause actuation of the identified motor in the direction opposite to the direction of the movement of the handle to generate the computed force in the direction opposite to the direction of the movement of the handle.

11. A robotic surgical system with user engagement monitoring, comprising:

a robot assembly including a robotic arm coupled to a surgical instrument;

a surgeon console including:
- a handle communicatively coupled to at least one of the robot assembly, the robotic arm, or the surgical instrument,
- a plurality of motors, wherein the plurality of motors are operably coupled to the handle and are associated with a plurality of directions, respectively, of movement of the handle, and
- a display device; and a tracking device including an image capture device configured to capture an image of a user position reference point, wherein at least one of the surgeon console or the tracking device is configured to:
- compute, based on the captured image, a position of the user position reference point relative to the display device,
- determine whether a user is engaged with or disengaged from the surgeon console based on the computed position,
- in response to the determination that the user is disengaged with the surgeon console:
  - cause the robotic surgical system to operate in a safe mode,
  - identify a first position of the handle,
  - compute a distance traveled by the handle from the first position of the handle,
  - compute a direction of the movement of the handle,
  - compute, based on the distance, a force in a direction opposite to the direction of the movement of the handle,
  - identify, among the plurality of motors of the handle, a motor associated with the direction opposite to the direction of the movement of the handle, and
  - cause actuation of the identified motor in the direction opposite to the direction of the movement of the handle to generate the computed force in the direction opposite to the direction of the movement of the handle, wherein the surgeon console is further configured to:
- actuate the motor in the direction opposite to the direction of the movement of the handle until the handle is positioned in the first position.

12. The robotic surgical system of claim 1, further comprising eyewear including a plurality of markers, wherein the user position reference point includes at least one of the plurality of markers.

13. The robotic surgical system of claim 1, wherein the user position reference point includes at least one of an eye, a head, or another portion of the user.

14. The robotic surgical system of claim 1, wherein the display device is an autostereoscopic display device.

* * * * *